US008496754B2

(12) United States Patent
Titmas (10) Patent No.: US 8,496,754 B2
(45) Date of Patent: Jul. 30, 2013

(54) METHODS AND APPARATUS FOR HYDROLYZING CELLULOSIC MATERIAL

(75) Inventor: James Titmas, Stow, OH (US)

(73) Assignee: Eau-Viron Incorporated, Gaylordsville, CT (US)

(*) Notice: Subject to any disclaimer, the term of this patent is extended or adjusted under 35 U.S.C. 154(b) by 622 days.

(21) Appl. No.: 12/452,605

(22) PCT Filed: Oct. 21, 2008

(86) PCT No.: PCT/US2008/011975
§ 371 (c)(1),
(2), (4) Date: Jan. 12, 2010

(87) PCT Pub. No.: WO2009/058204
PCT Pub. Date: May 7, 2009

(65) Prior Publication Data
US 2010/0121047 A1    May 13, 2010

(51) Int. Cl.
*C13K 1/02*           (2006.01)
(52) U.S. Cl.
USPC .............................................. 127/37; 127/1
(58) Field of Classification Search
USPC ........................................... 127/1, 37
See application file for complete search history.

(56) References Cited

U.S. PATENT DOCUMENTS

| | | | |
|---|---|---|---|
| 3,853,759 A | 12/1974 | Titmas | |
| 4,050,981 A | 9/1977 | Jamieson et al. | 162/37 |
| 4,342,831 A * | 8/1982 | Faber et al. | 435/163 |
| 4,792,408 A | 12/1988 | Titmas | 210/747 |
| 5,494,748 A | 2/1996 | Spehner | 428/379 |
| 5,711,817 A | 1/1998 | Titmas | 127/37 |
| 5,859,236 A | 1/1999 | Burkart | 536/56 |
| 5,865,898 A * | 2/1999 | Holtzapple et al. | 127/37 |
| 5,879,637 A | 3/1999 | Titmas | 422/129 |
| 6,716,360 B2 | 4/2004 | Titmas | 210/750 |
| 7,670,813 B2 * | 3/2010 | Foody et al. | 435/105 |
| 8,168,043 B2 * | 5/2012 | Titmas | 201/21 |
| 8,173,024 B2 * | 5/2012 | Titmas | 210/761 |
| 2006/0086673 A1 | 4/2006 | Titmas | 210/761 |
| 2007/0029252 A1 | 2/2007 | Dunson, Jr. | 210/603 |

OTHER PUBLICATIONS

Clark et al, Handbook of Green Chemistry and Technology, Blackwell Publishing (2002), pp. 389-390.*

* cited by examiner

*Primary Examiner* — David M Brunsman
(74) *Attorney, Agent, or Firm* — Renner, Kenner, Greive, Bobak, Taylor & Weber (57) ABSTRACT

A method of hydrolyzing woody cellulosic material containing lignin and air pockets involves impregnating the woody cellulosic material a first alkali having a pH of from 10 to 14 such that the first alkali is in contact with the lignin within the woody cellulosic material. Thereafter, the woody cellulosic material is advanced through a gravity pressure vessel for the acid hydrolysis conversion of cellulosic material to sugars. In accordance with other methods, ultrasound may be introduced during impregnation or at the gravity pressure vessel or both.

12 Claims, 9 Drawing Sheets

METHODS AND APPARATUS FOR HYDROLYZING CELLULOSIC MATERIAL

This application is a 371 national phase application of PCT Patent Application No. PCT/US2008/011975, filed Oct. 21, 2008, now abandoned, which is a non-provisional application of U.S. patent application Ser. No. 11/981,437, filed Nov. 1, 2007, now abandoned, which is incorporated herein by reference.

TECHNICAL FIELD

The present invention is generally directed toward a process whereby woody cellulosic material is converted to ethanol via acid hydrolysis of cellulosic material to sugars that are subsequently fermented. The acid hydrolysis takes place in a gravity pressure vessel. In particular, the present invention is directed to apparatus and methods for impregnating woody cellulosic material with an alkali to make it more amiable to treatment in the gravity pressure vessel. In more particular embodiments, this invention is also directed toward employing ultrasound in a gravity pressure vessel to aid in the processing of woody cellulosic material.

BACKGROUND OF THE INVENTION

Ethanol is a viable, economical, and relatively clean fuel substitute or additive. It is commonly obtained from the fermentation of grain or other substances containing sugars and starches. Less commonly, cellulosic material obtained from waste sources can be converted to sugars, which can then be fermented to obtain ethanol. The use of such waste cellulose has been particularly attractive in the face of higher grain costs and concerns about waste disposal. The use of grain for the production of ethanol places a demand on grain, increasing its costs for alternative uses. By employing cellulosic waste materials in the production of ethanol, it is possible to reduce the demand for fossil fuels and grain-derived fuels.

Cellulosic material generally includes waste paper, agricultural chafe, municipal solid waste residual fluff, and wood products. Source material containing cellulosic material is typically obtained from municipal solid wastes, generally after the extraction of marketable goods. Source cellulosic material, however, can be obtained from any of a number of sources.

Cellulosic material can be converted to sugar via hydrolysis. Heretofore in the art, cellulosic material has been hydrolyzed by first reducing the material to a pulp and then reacting that pulp with sulfuric acid. Upon the introduction of heat, hydrolysis begins and the cellulosic material is converted to sugar. The reaction is quenched by rapid cooling of the mixture, followed by acid neutralization. Rapid quenching is necessary because the hydrolysis reaction is virtually instantaneous, and overexposure to heat and acidic conditions will result in the decomposition of the sugar product thereby reducing yield.

Numerous methods and reactions for carrying out hydrolysis are known in the art. For example, U.S. Pat. Nos. 3,853,759, 4,792,408, 5,711,817, and 5,879,637 disclose continuously flowing hydraulic columns wherein materials suspended in water are heated and gravity pressurized to effect hydrolysis. The heated material is forced upwardly through the column by column pressure and thereby cooled and depressurized. U.S. Pat. Nos. 5,711,817 and 5,879,637 disclose hydraulic columns (also termed "gravity pressure vessels") for hydrolyzing cellulosic material, with means to control and manipulate the length of the hydrolysis reaction and control the quenching of the reaction. The present invention will be applicable particularly in the processes of those patents, but its application is not limited thereto or thereby.

The present invention is concerned mainly with the conversion of "woody" cellulosic material to useful end products through the use of a gravity pressure vessel and fermentation processes. Herein, "woody cellulosic material" is understood to refer to cellulosic materials containing a fibrous or woody matrix including variable percentages of heterogeneous components, including but not limited to: air pockets, lignin, glucan, moisture, xylan, ash or random metal oxides, uronic acids, arabinan, galactan, mannan, acetyl, soil, chlorophyll, proteins and other trace extracts as would be well known to those practiced in the arts. Though the gravity pressure vessel and related methods have been practiced with some success with other types of cellulosic material, difficulties have been encountered in the use of woody cellulosic material. Large amounts of energy are required to mechanically break down woody cellulosic material to expose the cellulosic material for the hydrolysis to sugars. The energy input to break the woody cellulosic material down to a size where free fibers can be converted to saccharides through weak acid hydrolysis can be significantly larger than the energy resulting from the ethanol produced from the cellulosic material. Additionally, air pockets in woody cellulosic materials can cause the materials to float in a carrier fluid through the gravity pressure vessel, preventing the materials from flowing through the system. As a result, such woody cellulosic materials either are not employed in the gravity pressure vessels or, to the extent that they might be so employed, are generally refractory to the existing arts.

The present invention seeks to satisfy the need in the art for a process for reducing the size of woody cellulosic materials fed to gravity pressure vessels, and seeks also to better suspend the woody cellulosic material in the carrier fluid of the gravity pressure vessel, in order to increase the efficiency of the process of converting the cellulosic material to ethanol via acid hydrolysis and fermentation.

SUMMARY OF THE INVENTION

In general, the present invention provides a method of hydrolyzing woody cellulosic material containing lignin and air pockets. In accordance with the method, woody cellulosic material is impregnated with a first alkali having a pH of from 10 to 14 such that the first alkali is in contact with the lignin within the lignin-containing woody cellulosic material. Thereafter, the woody cellulosic material is advanced through a gravity pressure vessel for the acid hydrolysis conversion of cellulosic material to sugars.

In accordance with other embodiments, this invention provides a method of hydrolyzing woody cellulosic material containing lignin and air pockets, wherein the method involves introducing woody cellulosic material into a gravity pressure vessel, and introducing ultrasound at the gravity pressure vessel. More particularly, the gravity pressure vessel includes (a) a tubular casing having a lower closed end, (b) a counterflow tubular casing positioned within the tubular casing and having an lower open end whereby an outer reaction annulus is formed between the tubular casing and the counterflow tubular casing, and (c) a starved oxidation reaction zone proximate the lower closed end of the tubular casing. The ultrasound is introduced at the starved oxidation reaction zone.

In yet another embodiment, this invention provides a method of hydrolyzing woody cellulosic material containing lignin and air pockets, wherein the method includes impregnating the woody cellulosic material with a first alkali having a pH of from 10 to 14 such that the first alkali is in contact with the lignin within the woody cellulosic material, and thereafter introducing woody cellulosic material into a gravity pressure vessel, and introducing ultrasound at the gravity pressure vessel. More particularly, the gravity pressure vessel includes (a) a tubular casing having a lower closed end, (b) a counterflow tubular casing positioned within the tubular casing and having an lower open end whereby an outer reaction annulus is formed between the tubular casing and the counterflow tubular casing, and (c) a starved oxidation reaction zone proximate the lower closed end of the tubular casing. The ultrasound is introduced at the starved oxidation reaction zone.

A preferred exemplary apparatus and method for the continuous conversion of cellulosic material to ethanol, which incorporates the concepts of the present invention, is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

FIG. 7 shows an elevational view and FIGS. 7A, B and C show sectional views of a paddle made in accordance with this invention for introducing streams of fluid for cleaning the gravity pressure vessel and for introducing ultrasound to the gravity pressure vessel;

PREFERRED EMBODIMENT FOR CARRYING OUT THE INVENTION

The overall process and system of the present invention is best described with reference to the schematic representation of FIG. 1. It should be understood, for purposes of this disclosure, particularly with regard to the schematic representation, that appropriate pumping devices and conduits are employed to move material between the various stages of the system. It should be further understood that the process which converts cellulosic material to ethanol is a continuous process, and therefore one of ordinary skill in the art will understand that various pumping devices and storage areas will be employed to maintain the process in continuous operation.

Figure 1:
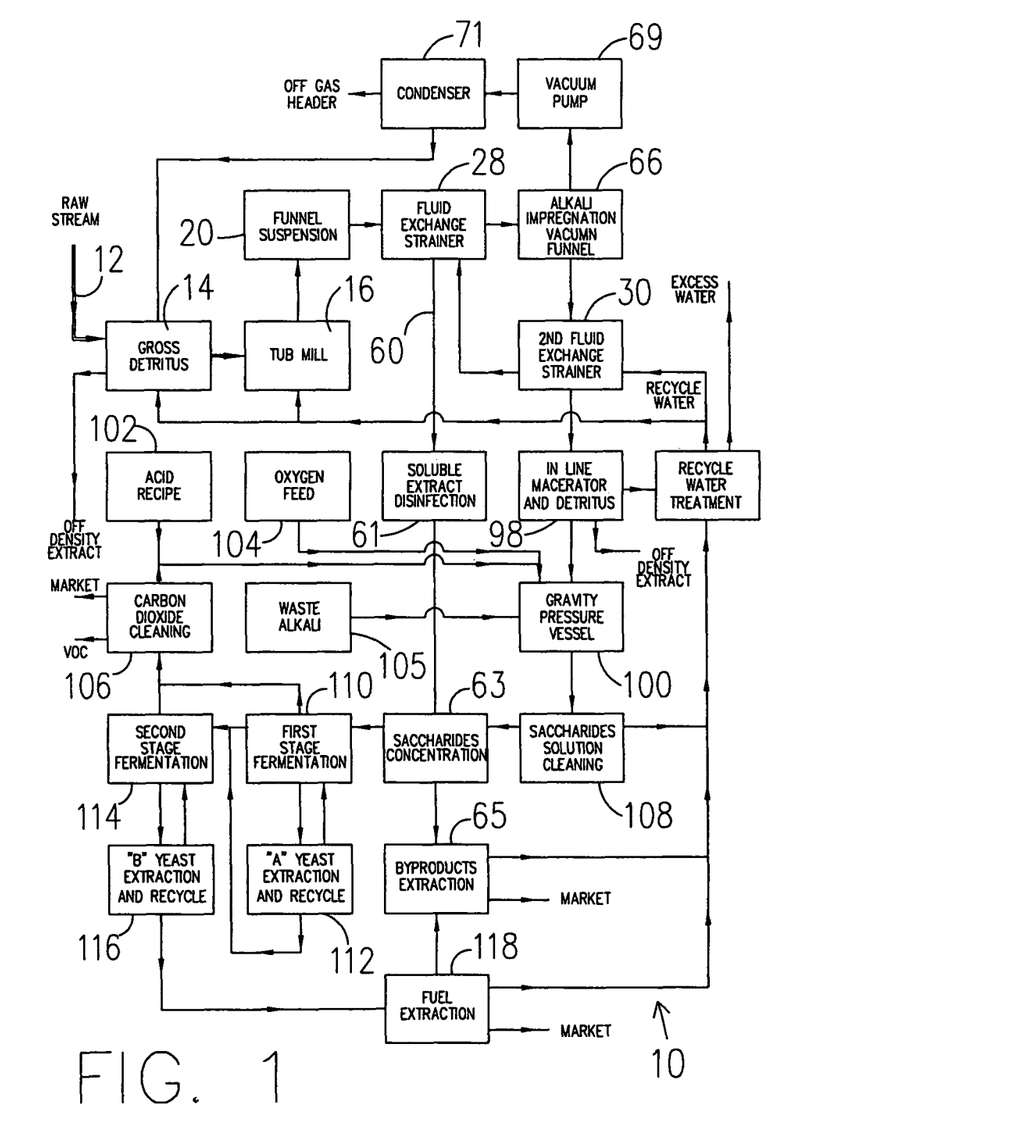
FIG. 1 is a flow chart of the overall process and system for producing ethanol from cellulosic material in accordance with this invention.

In the process generally designated in the schematic of FIG. 1 by the numeral 10, a raw material stream 12 of cellulosic material, undesired raw material and water is delivered to a detritus tank 14 where the cellulosic material is separated from undesired raw material in a known manner. The raw material stream includes woody or fibrous cellulosic material. In accordance with this invention, the woody cellulosic material can be obtained from any of a number of sources including but not limited to construction and demolition debris; agricultural wastes; yard wastes; wood products in or from manufacturing; storm damage debris; pulp and paper production wastes; bagasse; corn stover, and harvested fibrous crops. Because some of these types of materials generally have little value once designated as waste, they often present storage liabilities, and, commonly, persons with such materials will pay for their removal.

With the introduction of water as part of the raw material stream 12, some of the material might dissolve, while cellulosic material might suspend in the water as a slurry. The majority of the woody cellulosic material will float in the carrier water, making it difficult to carry it through the system. At detritus tank 14, undesired higher density materials such as sand or soil can be removed, while retaining the floating woody cellulosic material. Undesired higher density materials that have sunk in the carrier fluid can be removed.

From the detritus tank 14, the refined material stream of water and cellulosic material is delivered to a tub mill 16 where solids are reduced to a common smaller size. Generally, the solids are reduced to about 2×2×4 cm in size, or, more preferably, 1×1×2 cm in size along with other random finer materials, though the cost in energy to reduce the material to ever smaller pieces must be considered in light of the energy obtained from the end products of this process. At tub mill 16, there may be a second opportunity to remove undesirable materials that were attached to the cellulosic material in the process stream or were otherwise not removed in the detritus tank 14.

This invention focuses on treating woody cellulosic material so that it can be accessible to chemicals used to depolymerize holocellulosic materials and to flow through a gravity pressure vessel for the conversion of cellulosic material to ethanol. The woody cellulosic materials will not readily flow with the water through a gravity pressure vessel, and instead will float and frustrate the flow of the system. Thus, in this invention an alkali is introduced into the matrix of the woody cellulosic material to bring its density closer to and preferably slightly higher than the carrier water, therefore ensuring that a majority of the woody cellulosic material in the process stream will flow through the gravity pressure vessel and be efficiently processed. The target specific gravity of the materials in suspension to be processed would be 0.98 to 1.04, or more specifically between 1.00 and 1.02.

Figure 2:
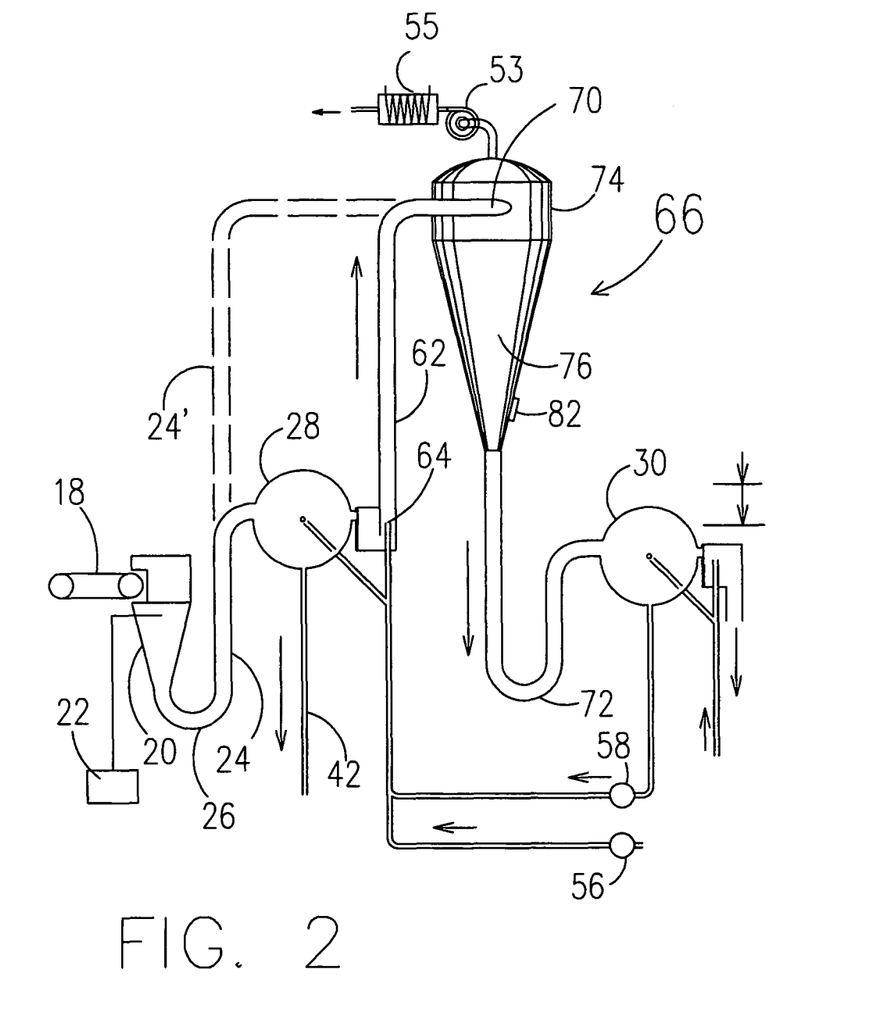
FIG. 2 is a general schematic diagram of the apparatus employed for introducing alkali fluids to the cellulosic material flowing through the system.

Referring now to FIG. 2, the cellulosic material exits the tub mill 16 on a scale conveyor 18, and is introduced to a covered emersion funnel 20. Water is also introduced to emersion funnel 20 from water source 22. The water and cellulosic material flow in conduit 24 from funnel 20, through trap 26, and into primary alkali fluid, strainer 28, with the movement taking place due to the hydraulic drop through the siphon system from an inlet at funnel 20 to an outlet at a secondary alkali fluid exchange strainer 30, explained more fully below. The hydraulic drop moves the cellulosic material and water, preferably creating a coriolis effect at funnel 20, sufficient to drag woody cellulosic materials through the conduit 24. This effect is sufficient to move the woody cellulosic material along with the water carrier fluid.

Figure 3:
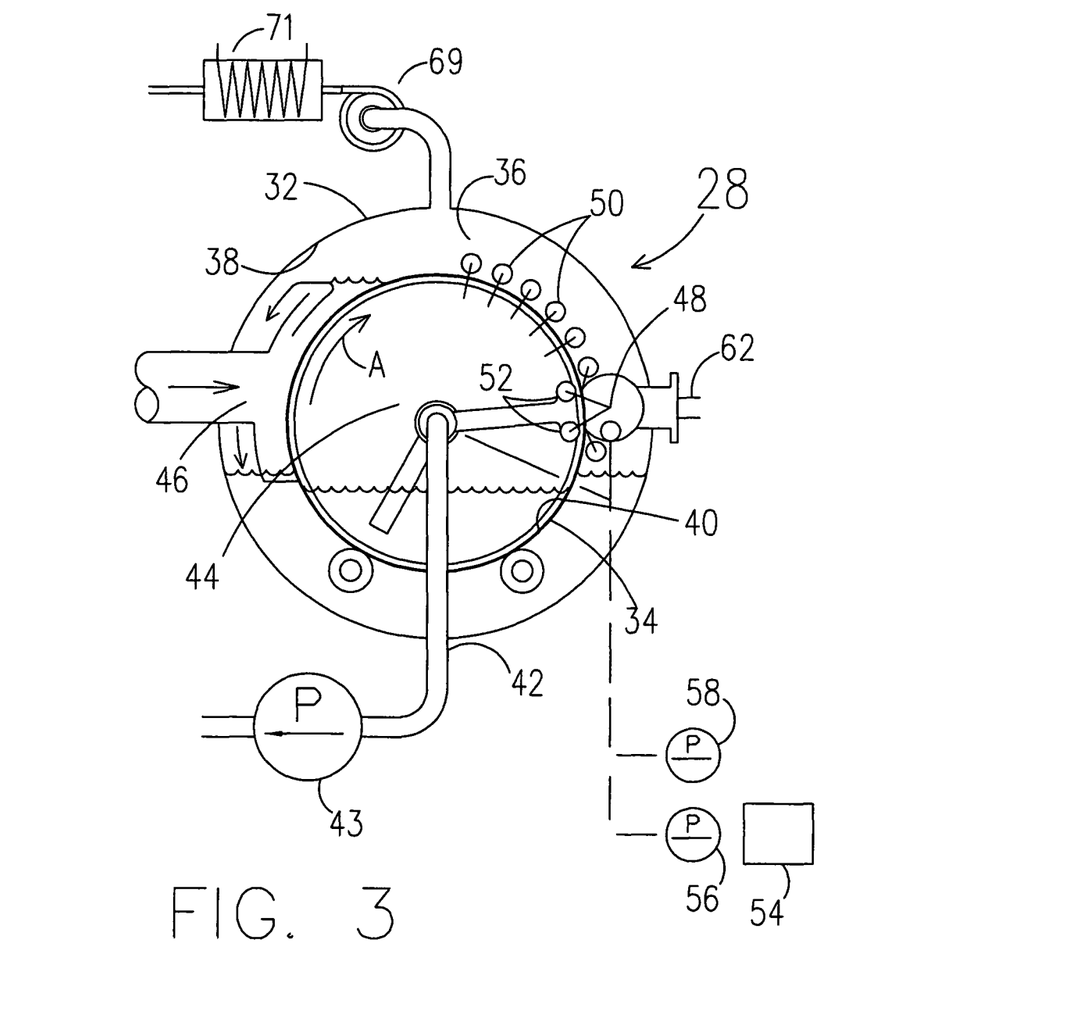
FIG. 3 is a general schematic diagram of the primary alkali fluid exchange strainer of FIG. 2.

At the primary alkali fluid exchange strainer 28, the water carrier fluid is substantially removed from the process stream and replaced with a primary alkali fluid. With reference to FIG. 3, it can be seen that primary alkali fluid exchange strainer 28 includes a main chamber 32 having a sieve drum 34 therein to create an annular space 36 between the wall 38 of the main chamber 32 and a perforated wall 40 of sieve drum 34. A conduit 42 communicates with the interior 44 of the drum 34 and may include a pump 43 to draw water with dissolved saccharides from the process stream, through perforated wall 40 and into the interior 44 to be drawn away through conduit 42. The drum 34 rotates in the main chamber 32 in the direction of arrow A, and cellulosic material introduced to the primary alkali fluid exchange strainer 28 coats the perforated wall 40 of the drum 34 and rides on the perforate wall 40, from an inlet 46 to an outlet chamber 48. Water is pulled out of the process stream by pump 43, and a plurality of rinse jets 50 direct de-aerated water over the cellulosic material and into the interior 44 of drum 22. De-aerated water is preferred so as to minimize any potential introduction of gasses into the system. Gases such as air extracted from the woody and fibrous materials do not condense and are removed via a blower 53 from the system so as to maintain vacuum conditions to sustain the siphon characteristics of conduits 24, 62 and 72 of FIG. 3 including the enclosed strainer 28, and the funnels 20 and 76. Water vapor is also extracted with the air which can condense by chilling in coil 55 and thus contribute to establishing and sustaining vacuum conditions in the siphon system.

At outlet chamber 48, a plurality of alkali jets 52 direct a primary alkali fluid over the cellulosic material riding on drum 34, directing the primary alkali fluid from the interior 44 of drum 34, through the perforated wall 40, thereby knocking cellulosic material off of the drum 34 and into the outlet chamber 48. In this way, the water is substantially removed from the process stream and is replaced by a primary alkali fluid. The term "primary alkali fluid" is used herein to distinguish the alkali fluid employed here from a "secondary alkali fluid" that is employed later in this process. With reference back to FIG. 2, the primary alkali fluid is fed, as needed, from a stock alkali source 54 and, in certain embodiments, from an optional recycling of the primary alkali removed from the process stream at the secondary alkali fluid exchange strainer 30, described more fully below. A pump 56 is employed to move the new alkali fluid from the stock alkali source 54 and a pump 58 is employed to move the recycled alkali fluid from the strainer 30.

The primary alkali fluid is chosen for its ability to dissolve lignin within the matrix of the woody cellulosic material, thereby causing it to break down to even smaller pieces, preferably to small separated fibers, exposing more surface area of the cellulosic material. The woody cellulosic material will begin to broom as the lignin is dissolved, and fibers will slough off. The cellulosic material is ultimately fed to a gravity pressure vessel. At the gravity pressure vessel, the dissolved lignin will be oxidized by oxygen in the carrier fluid, and the oxidation, being exothermic, will provide heat to bring the process stream closer to the target temperature for an acid hydrolysis de-polymerization of the cellulosic material. The acid hydrolysis will be improved by the fact that the woody cellulosic material will be broken down to small separated fibers.

It will be most useful to employ this strainer 28 when the cellulosic material feed stock is of a type that contains considerable amounts of starches and sugars that are soluble or colloidal in nature (for example arabinose or xylose) that can be easily extracted by the carrier fluid, which will typically be water. For such feed stocks, the strainer 28 will remove much of those easily extracted starches and sugars along with the carrier fluid, and the starches and sugars so removed can be fed to additional process apparatus, as represented in FIG. 1, at arrow 60 or, in FIG. 2, at conduit 42. It should be appreciated that the water is to be substantially removed, so that the sugars and starches in the water are efficiently recovered for their use in the fermentation process after sterilization by ultraviolet radiation or other suitable non-chemically invasive means.

Referring again to FIG. 1, it can be seen that any useful soluble extracts removed at primary alkali fluid exchange strainer at conduit 42 can be fed to a soluble extract disinfection station 61 to remove or render harmless invasive bacteria that would interfere with optimal fungi metabolism to produce ethanol or other pre-selected products of metabolism. After any necessary disinfecting, the soluble extracts can be advanced to a saccharides concentration station 63 to increase the concentration of the saccharides therein, with any marketable byproducts being extracted as at 65. The concentrated saccharides can be fed to a known fermentation process, as shown a first stage fermentation 110. The strainer 28 thus provides an initial starch and sugar recovery stage, with the starches and sugars being treated in fermentation processes to create useful products, particularly ethanol. This strainer 28 is most beneficially used with feed stocks containing enough starches and sugars of a type that can be removed at strainer 28 to justify the use of the additional process equipment. More particularly, strainer 28 would not be beneficial if the energy used to extract the starches and sugars at strainer 28 and move and treat those sugars to obtain ethanol is more than the energy obtained from the ethanol and other products produced. When dealing with cellulosic material feed stocks that do not contain considerable amounts of starches and sugars for removal at a strainer 28, the primarily alkali fluid can be added directly at siphon 20, and the strainer 28 can be removed from the process. This is shown in FIG. 2, at the elements drawn in dashed lines, particularly at conduit 24'; and alkali feed lines 57 and 59, would provide the primary alkali fluid directly to siphon 20.

After the process stream passes through the primary alkali fluid exchange strainer 28, with the water being substantially removed and replaced with a primary alkali fluid, the process stream enters the siphon feed pipe 62, where additional primary alkali is received, as shown at inlet 64. The process stream flowing through siphon feed pipe 62 is now referred to as including primary alkali fluid and cellulosic material, as those are the main components.

The primary alkali fluid is chosen and added so that the process stream advancing through siphon feed pipe 62 is characterized by having a pH of from about 10 to 14, more preferably from about 11 to 13. A sensor can be employed at outlet chamber 48 to read the pH of the process stream, and a microprocessor 51 can be programmed to adjust the amount of stock and recycled alkali fluid added. Typically, the primary alkali fluids will be aqueous fluids, though solvents other than water might be beneficially employed for particular cellulosic material feed stocks, and this invention is not limited to aqueous alkali fluids. Useful bases for the provision of the primary alkali fluids may be selected from calcium oxides or other non-toxic metal oxide alkalis known to precipitate on neutralization with carbonic or sulfuric acids, but excluding components that would produce fermentation inhibitors or accumulate in re-circulating water systems such as chlorides or toxic metals such as lead or mercury. Particularly useful base is calcium hydroxide.

Referring back to the schematic of FIG. 1, and with continued reference to FIG. 2, the process stream of cellulosic material and primary alkali fluid is fed from the alkali fluid exchange strainer 28 to an inverted funnel 66, through the siphon conduit 62. At funnel 66, the alkali is caused to enter into the matrix of the woody cellulosic material, particularly to contact the lignin in the woody cellulosic material. As seen in FIG. 2, a vacuum source 68 acts on funnel 66 and serves to remove air from the woody cellulosic material therein. Gases such as air extracted from the woody and fibrous materials do not condense and are removed via a blower 69 from the system so as to maintain vacuum conditions to sustain the siphon characteristics of conduits 24, 62 and 72 of FIG. 3 including the enclosed strainer 28, and the funnels 20 and 76. Water vapor is also extracted with the air which can condense by chilling in coil 71 and thus contribute to establishing and sustaining vacuum conditions in the siphon system. The vacuum source 68 preferably establishes a pressure of less than 1 atmosphere in the funnel 66, more preferably from 0.7 to 0.2 atm, and even more preferably from 0.5 to 0.2 atm. These pressures are likely to be sufficient for removing air pockets within aerated cellulosic material, but their disclosure here is not to be read as limiting this invention.

As the process stream flows through the funnel 66, from the siphon inlet 70 to the trap 72, the space previously occupied by the air in the woody cellulosic material is at least partially displaced with the primary alkali due to the pressure increase resulting from the drop in height. Preferably the funnel assembly 66 is sized such that the pressure increase from inlet 70 to the bottom of trap 72 is at least 1.3 atmosphere.

The funnel 66 is preferably shaped with a generally cylindrical upper portion 74 and a frustoconical lower portion 76, and inlet 70 introduces the process stream tangentially to the cylindrical upper portion 74 to help reinforce a coriolis effect (clockwise in the northern hemisphere and counterclockwise in the southern hemisphere). This preferred flow helps induce submergence of residual partially floating debris in the fluid stream of primary alkali and cellulosic material.

Optionally, an ultrasound driver 82 can be positioned to introduce ultrasonic waves in funnel assembly 66. The ultrasound will agitate the process stream and thereby help to improve gas extraction and the rate at which alkali enters the matrix of the woody cellulosic material, thus increasing the rate at which the lignin can be dissolved by the alkali. This increases the brooming of the woody cellulosic material and its separation into smaller fibers that can be de-polymerized to saccharides through acid hydrolysis. Virtually any ultrasonic wave can be introduced to the siphon 66, though, in particular embodiments the ultrasonic wave has a power density of 23 W/square cm+/−10% and a frequency of from 24 kHz to 45 kHz and more specifically between 26 kHz and 30 kHz plus harmonics thereof. Preferably, the residence time of the process stream is such that the process stream is exposed to the ultrasound for a period of from 2 to 10 seconds, more preferably from 3 to 5 seconds.

Figure 4:
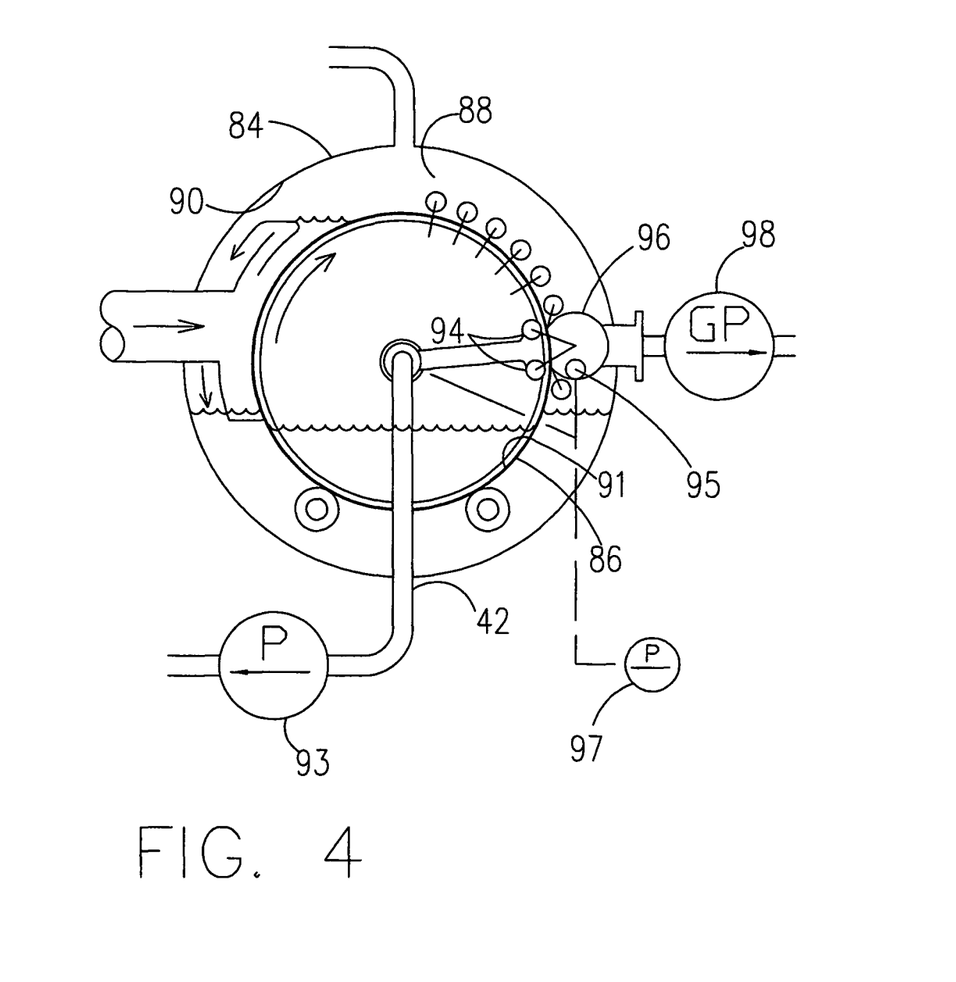
FIG. 4 is a general schematic diagram of the secondary alkali fluid exchange strainer of FIG. 2.

The process stream of cellulosic material and primary alkali carrier fluid moves through the sealed system from outlet chamber 48 to secondary alkali fluid exchange strainer 30 by means of the hydraulic drop. The secondary alkali fluid exchange strainer 30 is substantially similar to the primary alkali fluid exchange strainer 28, but introduces a secondary alkali rather than a primary alkali. As will be described more fully below, the strainer 30 is employed to bring the pH of the process stream down to a more neutral level useful in the gravity pressure vessel. Referring to FIG. 4, secondary alkali fluid exchange strainer 30 includes a main chamber 84 having a sieve drum 86 creating an annular space 88 between the wall 90 of main chamber 84 and a perforated wall 91 of drum 86. At secondary alkali fluid exchange strainer 30, the primary alkali carrier fluid is removed by conduit 92 and pump 93, and a new, secondary alkali fluid is introduced at secondary alkali jets 94 at outlet chamber 96. Notably, it is the primary alkali carrier fluid that is substantially removed, while the primary alkali within the matrix of the woody cellulosic material remains. The cellulosic material is carried to the next apparatus of the process 10 with the secondary alkali as the carrier fluid, though, as with primary alkali fluid exchange strainer 28, some primary alkali may remain. The process stream exiting strainer 30 preferably includes very little primary alkali fluid, so that less secondary alkali is necessary to bring the process stream to the desire target pH level.

The primary alkali fluid is selected to be a strong base suitable for maintaining a pH of from about 10 to 13 in the matrix of the woody cellulosic material. This is suitable for breaking down the lignin in the woody cellulosic material to make the woody cellulosic material more susceptible to being broken down into separated cellulosic fibers. However, the cellulosic material in this process stream will ultimately be subjected to an acid hydrolysis reaction in a gravity pressure vessel. Thus, the secondary alkali is selected to be a weaker base than the primary alkali, so that less acid will have to be added to the process stream of cellulosic material and secondary alkali in order to bring about wet acid hydrolysis in the gravity pressure vessel.

The secondary alkali fluid is chosen and added so that the process stream advancing to the gravity pressure vessel is characterized by having a pH of from about 7 to 8.5, more preferably from about 7.8 to 8.2. A sensor can be employed at outlet chamber 96 to read the pH of the process stream, and a microprocessor can be programmed to adjust the amount of secondary alkali fluid added. Typically, the secondary alkali fluids will be aqueous fluids, though solvents other than water might be beneficially employed for particular cellulosic material feed stocks, and this invention is not limited to aqueous alkali fluids. Useful bases for the provision of the secondary alkali fluids may be selected from calcium oxides or other non-toxic metal oxide alkalis known to precipitate on neutralization with carbonic or sulfuric acids, but excluding components that would produce fermentation inhibitors or accumulate in re-circulating water systems such as chlorides or toxic metals such as lead or mercury. Particularly useful base is calcium hydroxide.

With reference back to FIG. 1, the process stream continues from strainer 30 to the gravity pressure vessel 100. The cellulosic material in the process stream will have a tendency to agglomerate together, and, therefore, before the gravity pressure vessel 100, the process stream may be fed to an in-line macerator 98, where these agglomerates can be broken up. Additionally, the cellulosic material can be further macerated to smaller, more useful sizes, and additional efforts can be made to remove any undesired materials in the process stream. The process stream exiting the strainer 30 or in-line macerator 98, if one is used, will preferably be of the aforementioned pH condition having a suspended solids content between 8% and 16% and more commonly between 10% and 14% as dictated by variable field conditions and the average gravity pressure vessel temperature (viscosity) of the carrying medium.

Within the gravity pressure vessel 100, which will hereinafter be described in more detail, the processed process stream is subjected to proper conditions for carrying out acid hydrolysis. This hydrolysis converts a significant portion of the cellulosic material to sugars. It should be appreciated that the resulting sugars become part of the process stream following hydrolysis. For purposes of this description, the term sugars will generally refer to those products resulting from the acid hydrolysis of cellulosic materials, typically definable as sugars and starches and derivatives thereof. It should be appreciated, however, that a very broad spectrum of resultant materials may result from hydrolysis, even when closely controlled feed stocks are employed.

Acid, oxygen, alkali and carbon dioxide are fed to the gravity pressure vessel 100. This is generally shown at acid recipe 102, oxygen feed 104, alkali feed 105 and carbon dioxide cleaning 106 and the arrows associated therewith in FIG. 1. In the gravity pressure vessel 100 the woody cellulosic material is broken down and both woody and non-woody cellulosic material is converted to saccharides, thus creating a saccharide solution. The saccharide solution is cleaned as at 108, for example, through density separators and filters. Thereafter, if necessary, the saccharide solution is concentrated as at 63 (along with saccharides, if any, extracted in the primary alkali fluid exchange strainer 28), for example, through the use of reverse osmosis filters or molecular sieves. The concentrated saccharide solution is then fed to fermentation stages, with exemplary fermentation stages shown here as first stage fermentation 110, with a first "A" yeast extraction and recycle station 112, and second stage fermentation 114, with a second "B" yeast extraction and recycle station 116. The resultant ethanol fuel is extracted, as are byproducts and water, as shown at fuel extraction 118 and the arrows associated therewith in FIG. 1. Similarly, carbon dioxide, volatile organic compounds, and other marketable compounds including but not limited to, furfural, urea, acidic acid, formic acid, xylose, calcium carbonate, saccharides, yeast, aggregate and metal ores can be extracted from the processes and either appropriately processed and taken to market or fed back to appropriate areas of the process of FIG. 1, as shown at carbon dioxide cleaning 106.

The use of the gravity pressure vessel to produce the desired saccharides is generally known, as is the fermentation process and the various processes for either recovering reagents for recycling into the system or recovering marketable products or waste products. Methods for saccharide production in a GPV are provided in U.S. Pat. Nos. 5,711,817 and 5,879,637, and this invention is not particularly concerned with the disclosure of the particulars of the GPV practice. Rather, this invention improves upon the known gravity pressure vessel arts by providing a way to employ woody cellulosic material in a GPV and increase the efficiency of the processes occurring in the GPV. The above disclosure teaches how to condition woody cellulosic material with alkali fluids so that it may readily flow through the GPV without the need for energy-consuming pumps. Mention has been made that the alkali fluid can be chosen to help to break down the woody cellulosic material as well, and the following disclosure will teach how ultrasound can be used to break down the cellulosic material in the GPV to achieve a more efficient acid hydrolysis. The following disclosure also explains the advantageous treatment of the lignin dissolved by the primary alkali fluid.

As previously described, the process stream from the secondary alkali fluid exchange strainer 30 is fed to the gravity pressure vessel 100. Gravity pressure vessels and their operation for treating cellulosic materials are generally known, and the specifics of a gravity pressure vessel need not be repeated here. Rather, the general structure will be disclosed so that the advances in the GPV process provided by this invention can be focused upon. Thus with respect to FIGS. 5 and 6, GPV 100 includes reactor vessel 150 having an outer reaction annulus 157 formed between a tubular casing 153 and couterflow tubular casing 156. An inner reaction annulus 165 is formed between tubular casing 156, which is open ended, and carbon dioxide input tube 160. An inner reactor casing 170 is provided in inner reaction annulus 165, and is removably attached to a portion of the vertical length of carbon dioxide input tube 160. The inner reactor casing 170 modifies the shape of inner reaction annulus 165 and creates and defines reaction areas.

Figure 5:
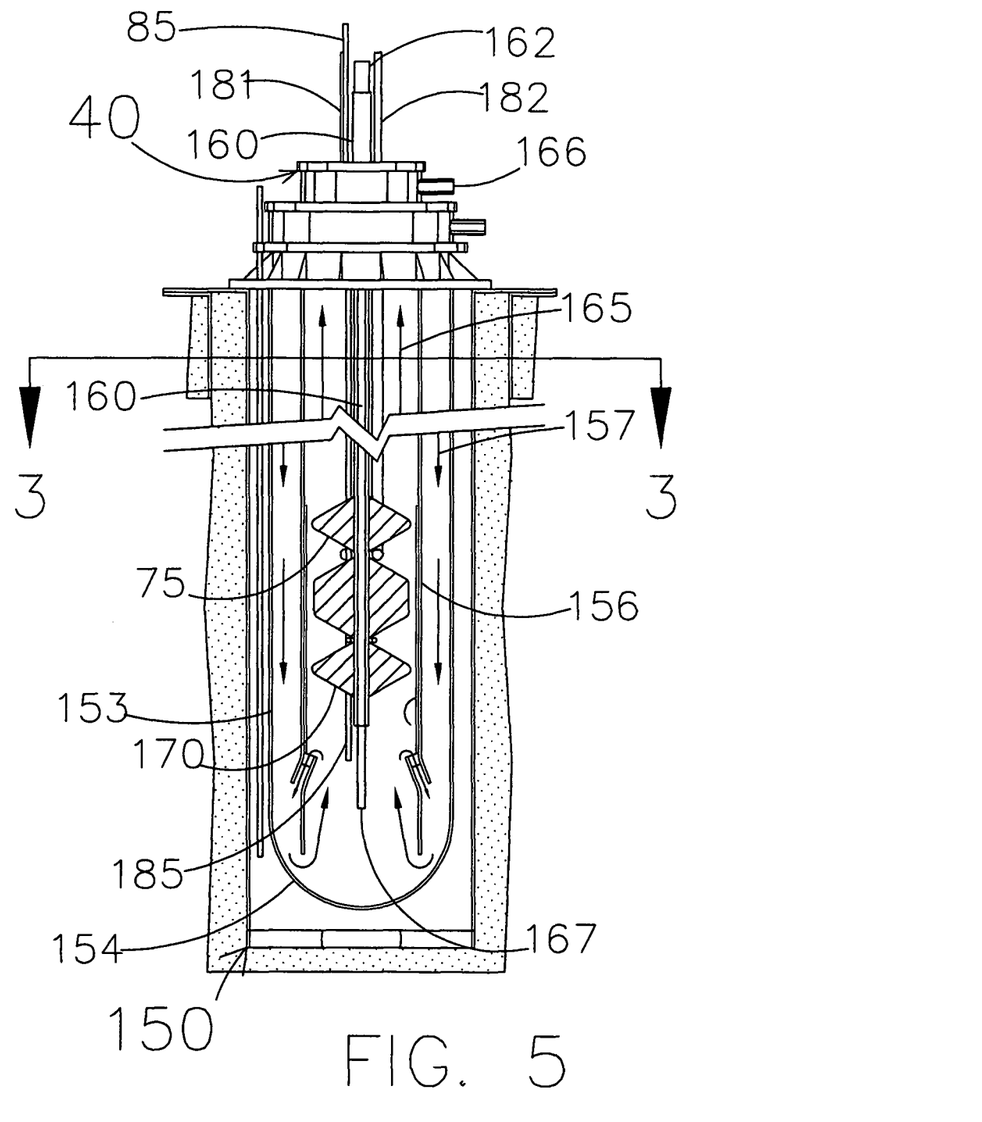
FIG. 5 is a fragmented vertical, cross-sectional view of a gravity pressure vessel in accordance with this invention.
Figure 6:
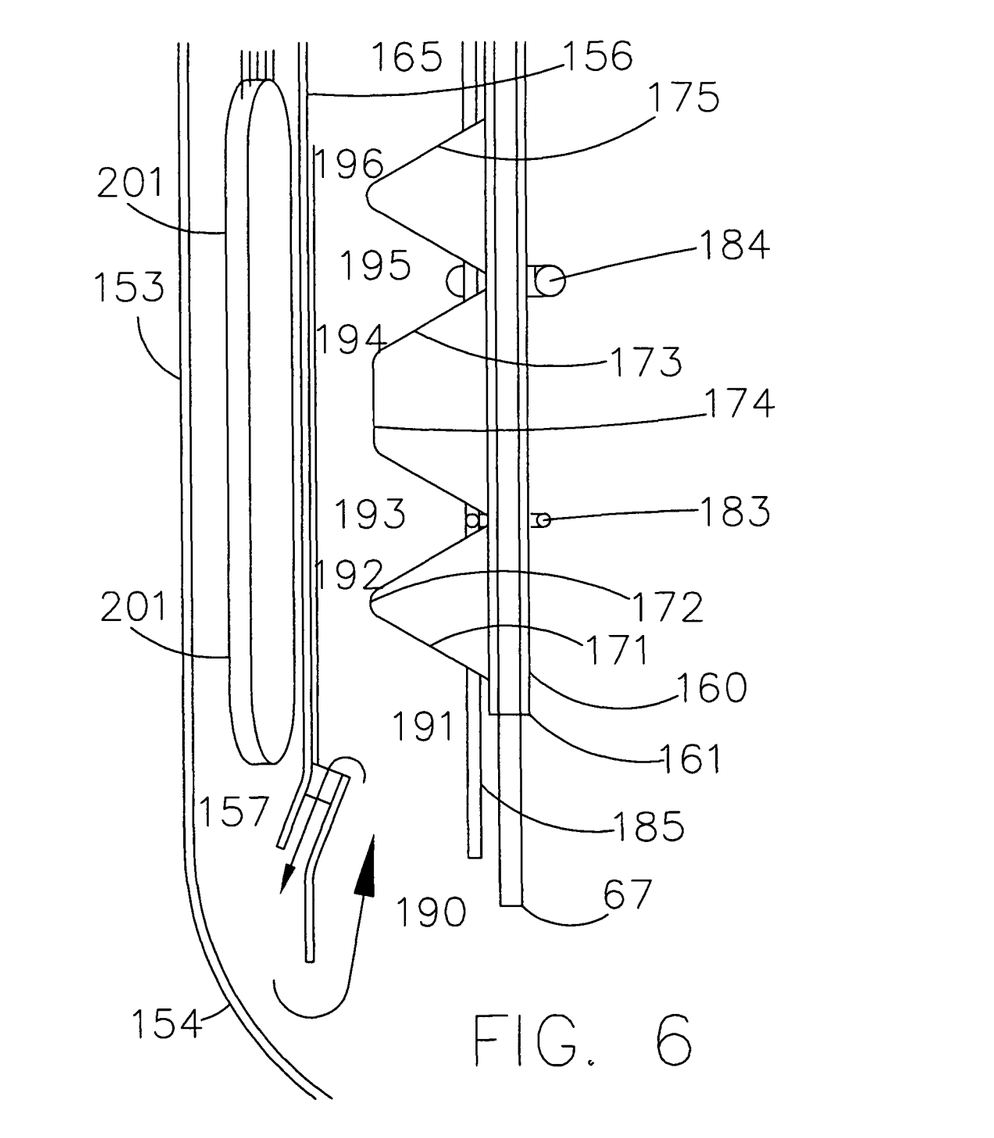
FIG. 6 is an isometric view of a portion of the gravity pressure vessel exposing the inner reactor casing.

The process stream descends and reaches the closed end 154 of casing 153, at region 190, which is a starved oxidation reaction zone. As it descends, the woody cellulosic material continues to break down as the lignin is dissolved by the primary alkali fluid within the matrix of the woody cellulosic material. This results in the presence of a substantial amount of dissolved lignin in the process stream. Additionally, as the woody cellulosic material breaks down, more cellulosic material is exposed for hydrolysis during ascension through the gravity pressure vessel. In the prior art, steam was typically added at region 190 to deliver heat to the process stream. However, in accordance with this invention, which includes the use of woody cellulosic material, oxygen is typically introduced down pipe 162 to discharge point 167. This will be described more fully below.

From region 190, the process stream ascends through inner reaction annulus 165, past the inner reactor casing 170 and through the reaction zones defined thereby. In this embodiment, inner reactor casing 170 includes first venturi section 171, second venture section 173, and third venture section 175. For purposes of explaining the hydrolysis of cellulosic material ascending through inner reaction annulus 165, these venturi sections are considered to define six reaction regions.

The first region 191 is generally defined as that region of annulus 165 below point 172 of first venturi section 171. At or near first reaction region 191, the carbon dioxide input tube 160 terminates at discharge point 161, to introduce the carbon dioxide to the process stream in region 191. This relates to the schematic of FIG. 1 and the introduction of carbon dioxide as at 106. The carbon dioxide forms carbonic acid within the process stream thereby lowering the pH and catalyzing the hydrolysis reaction. It is preferred that enough carbon dioxide be added to the process stream to bring the pH of the solution below 5.0 and preferably below 3.5. Because of the pressure resulting from the height of the process stream descending down outer reactor annulus 157 and the reduction in the density of the fluid resulting from the introduction of carbon dioxide, the process stream is caused to ascend up inner reactor annulus 165.

The preheated process stream, now containing sufficient carbon dioxide, continues to ascend up annulus 165 and encounters the second reaction region 192 where the flow of the fluid stream is restricted due to first venturi section 171. The process stream's contact with venturi section 171 creates a minor shock wave in the passing fluid that is a source of instantaneous mixing of the fluid and suspended particles.

Moving upward through annulus 165, the fluid stream next enters third reaction region 193. Region 193 is generally defined as the area within annulus 165 adjacent to or near the junction of first venturi section 171 and second venturi section 173. Within region 193, acid is introduced to the system through acid feed pipe 181 and acid feed collar 183, to achieve a pH in the range of about 2.0 to about 3.0, which carries out hydrolysis of the cellulosic materials. This relates to the schematic of FIG. 1 and the introduction of acid as at acid recipe 102.

As acid hydrolysis reactions convert the cellulosic material to sugars, the fluid stream continues up annulus 165 and enters forth reaction region 194. Region 194 is generally defined as the area within annulus 165 adjacent to and reduced as a result of cylindrical member 174 of second venturi section 173. Region 194 is restricted to increase the flow rate of the fluid stream undergoing acid hydrolysis, thereby limiting the time in which hydrolysis takes place. Extended acid hydrolysis of the cellulosic material beyond the required time will destroy the sugars that are sought from the reaction. Typically, it will take about 2 to about 4 seconds for the fluid stream to ascend through region 194. Because the reaction time is critical and may vary on several factors including the nature of the feed stock, the length of region 194, and therefore the reaction time, can be changed, by changing the dimension of member 174.

Moving rapidly through region 194, the fluid stream then ascends into the fifth reaction region 195. Region 195 is generally defined as the area within annulus 165 adjacent to or near the junction of second venturi section 173 and third venturi section 175. Within region 195, caustic solution, such as calcium hydroxide, is introduced via a caustic feed pipe 182 and caustic feed collar 184. This relates to the schematic of FIG. 1 and the introduction of alkali as at 105. The introduction of caustic solution raises the pH to approximately 7.5 or greater, thereby quenching the acid hydrolysis reaction, as known. The alkali addition at 105 is termed "waste" alkali because it may be provided from recovered primary alkali from the strainer 28, though it could also be provided from a different source.

Ascending toward the top of reactor vessel 150, the fluid stream is again restricted in sixth reaction region 196 due to third venturi section 175 which creates shock wave mixing. Continuing to move upward from this region, the fluid ascends unrestricted up the remainder of annulus 165 and eventually reaches the top of the reactor vessel 150 where it exits the vessel at outlet 166.

The general structure and functioning of a gravity pressure vessel has been disclosed above, and the advances of the present invention are now disclosed. As mentioned, in accordance with this invention, oxygen is introduced in region 190 by means of a pipe 162, where, in the prior art, it was typical to add steam. The oxygen is added to oxidize materials in solution, including particularly the lignin, and, thus, this is a starved oxidation reaction zone, wherein, by "starved oxidation reaction zone" it is meant that less oxygen is supplied than would be required to fully oxidize all of the organics in solution or suspension and sufficient oxygen is supplied to produce the required thermal gain to sustain autogenic gravity pressure vessel operation. The lignin and other materials will oxidize as the process stream ascends through inner reaction annulus 165, and this exothermic reaction will heat the up-flowing process stream, which will, in turn heat the down-flowing process stream as well. Thus, while steam was added proximate region 190 in the prior art, oxygen can be added in this process dealing with woody cellulosic material and significant amounts of lignin in solution. Steam might still be needed if the oxidation of lignin is not producing enough heat to bring the down-flowing process stream to the desired temperature. Steam might also be needed during a cold start of the present system. Thus, pipe 162 is to deliver either oxygen or steam or both, as needed. The oxygen will be added in an amount less than the stoichiometric amount needed. The amount of oxygen desired is field selected as dictated by the flow rate of the fluid medium, the age of the gravity pressure vessel operations accounting for strata warming and lower GPV radiant losses, the amount of lignin present in the feed materials, the variable rate of heat recovery through the GPV internal heat transfer tubular and the desired terminal temperature difference between the GPV fluids input and output.

It is desired that the process stream reach a temperature of from about 250° C. to 260° C. by the time it reaches region 190. Thus, a thermocouple tubular housing 185 may be employed to monitor the physical and chemical characteristics of the continuously flowing fluids within reactor vessel 150, and a microprocessor may be used to control the addition of oxygen or steam or both through pipe 162, based upon readings taken at the housing 185. Once the vessel is in continuous operation, heat resulting from the oxidation of lignin and the acid hydrolysis reactions migrates through counterflow casing 156 to heat the process stream as it descends down outer reactor annulus 157. Thus, steam is delivered through pipe 162 only on an as needed basis; that is, to compensate for that portion of downflowing fluids insufficiently preheated though counterflow 156.

It should be appreciated that the heat needed to drive a hydrolysis reaction of cellulosic material is generally greater than 200° C. and preferably in the range between about 260° C. and about 290° C. The greater the temperature, the less acid is needed to drive the reaction. At too great a temperature, however, the hydrolysis reaction is not easily controlled, and, therefore, results in the decomposition of the sugar product. Thus, based on the teachings herein, one of ordinary skill in the art will be able to alter the temperature and acidity level to achieve optimal results. Of course, the constantly changing feed stream will also factor into the optimal temperature and acidity sought. It should further be appreciated that the pressure experienced by the process stream within the gravity pressure vessel increases as the process stream approaches the bottom of the vessel. This increased pressure, which is generally in the range of between about 600 psi and about 1200 psi, and preferably between about 800 psi and about 1000 psi, further serves to drive the hydrolysis reaction.

To better employ the woody cellulosic material in the gravity pressure vessel, ultrasound is introduced to help break down the woody cellulosic material. The ultrasound is introduced to affect the down-flowing process stream in the outer reaction annulus 157, and is introduced at a point where the process stream has reached a temperature of at least 280 C. This will typically be in or very near region 190, which is proximate the bottom of the annulus 157. The ultrasound is preferably applied continuously. Ultrasound can be applied in any manner, though this invention provides specific paddle structures to provide the ultrasonic treatment. Virtually any ultrasonic wave can be introduced to the gravity pressure vessel, though in particular embodiments the ultrasonic wave has a power density of 23 W/square cm+/−10% and a frequency of from 24 kHz to 45 kHz and more specifically between 26 kHz and 30 kHz plus harmonics thereof. Preferably, the residence time of the process stream is such that the process stream is exposed to the ultrasound for a period of from 2 to 10 seconds, more preferably from 3 to 5 seconds.

In U.S. Pat. No. 5,080,720, a paddle is disclosed that includes cleaning nozzles for cleaning the annuli in a gravity pressure vessel, as, for example, at the outer reaction annulus 157 and the inner reaction annulus 165 in the gravity pressure vessel 100. In an embodiment of this invention, additional functional elements are provided in such a paddle. Particularly, ultrasound transducers are provided in the paddle in order to introduce ultrasound into the gravity pressure vessel to aid in breaking up the fibrous structure of the woody cellulosic material. Additional improvements are made to the paddle as well.

Figures 7, 7A, 7B, 7C:
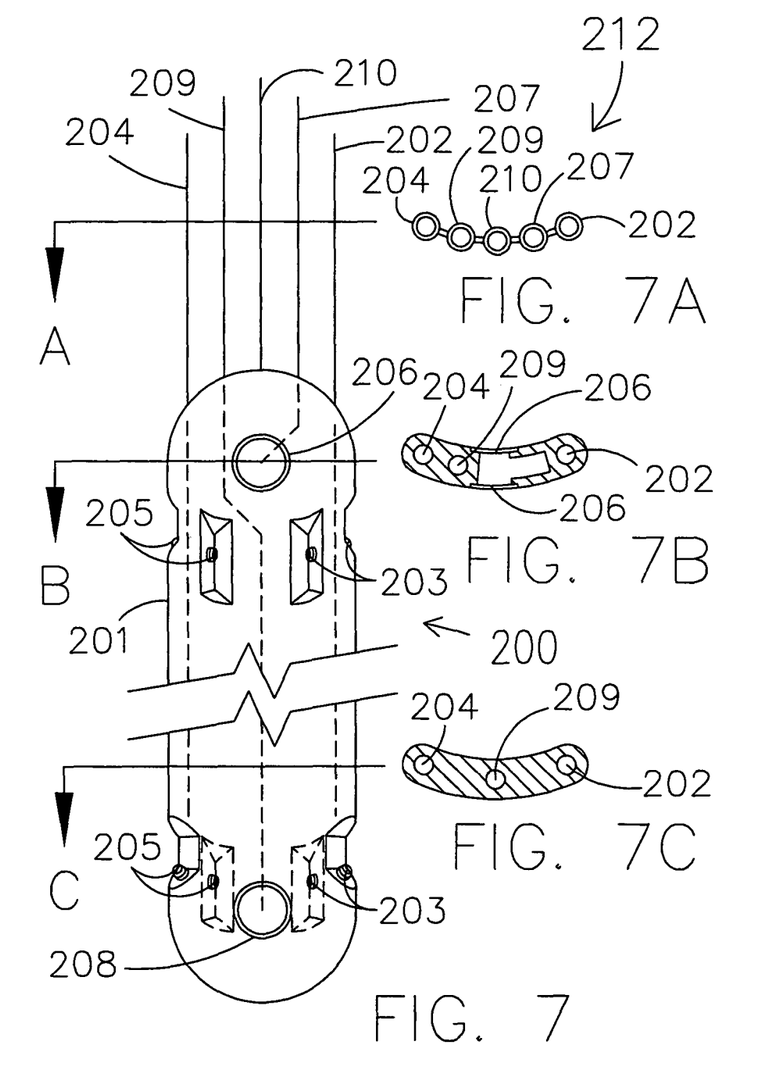

With reference to FIG. 7, a paddle is shown and designated by the numeral 200. The paddle 200 disclosed here is to be used to introduce ultrasound to the process stream as it flows down the gravity pressure vessel 100, at outer reaction annulus 157. This paddle 200 is therefore supported within the gravity pressure vessel 100 by the various tubes and cables that provide necessary functionality to various elements of the paddle 200, as will become more apparent below.

Paddle 200 has a body portion 201, and a pair of feed tubes 202 and 204 supply alternating fluid streams through passages in body portion 201 for the purpose of delivering fluid for cleaning the annulus 157 at respective cleaning heads 203, 205. The feed tubes 202 and 204 can be carried on a reel (FIG. 9) positioned above the gravity pressure vessel so that they may be raised and lowered, as desired. Moreover, the tubes 202 and 204 are flexible in nature so that, as will hereinafter be described, they may freely swing. The body portion 201 includes appropriate valves, fluid paths and nozzles to create fluid spray fan jets that both clean the walls defining the annulus of the gravity pressure vessel and, at the same time, impart a jet like or thrust force causing the paddle to move in desired directions within the annulus. This cleaning function is generally known, as, for example, by the disclosures within U.S. Pat. No. 5,080,720.

The paddle 200 further includes an upper ultrasound transducer 206 and lower ultrasound transducer 208, each controlled through appropriate feeds through their respective tubulars 207, 209. These transducers 206, 208 receive transducer pulse controls from a central processing unit, as known, and thereby deliver ultrasound to desired locations in the gravity pressure vessel 100. Cathodic protection is provided for the paddle 200 at anode 210. These various tubular feeds (feed tubes 202, 204, tubulars 207, 209, and anode 210) are secured together as a tube ribbon assembly, shown at numeral 212. A stitch welding of the neighboring tubulars, represented at 214, is preferred for creating the tube ribbon assembly 212. This welded linkage between the small diameter tubular components will mitigate the tendency for them to become entangled as they are moved throughout the gravity pressure vessel 100.

Figure 9:
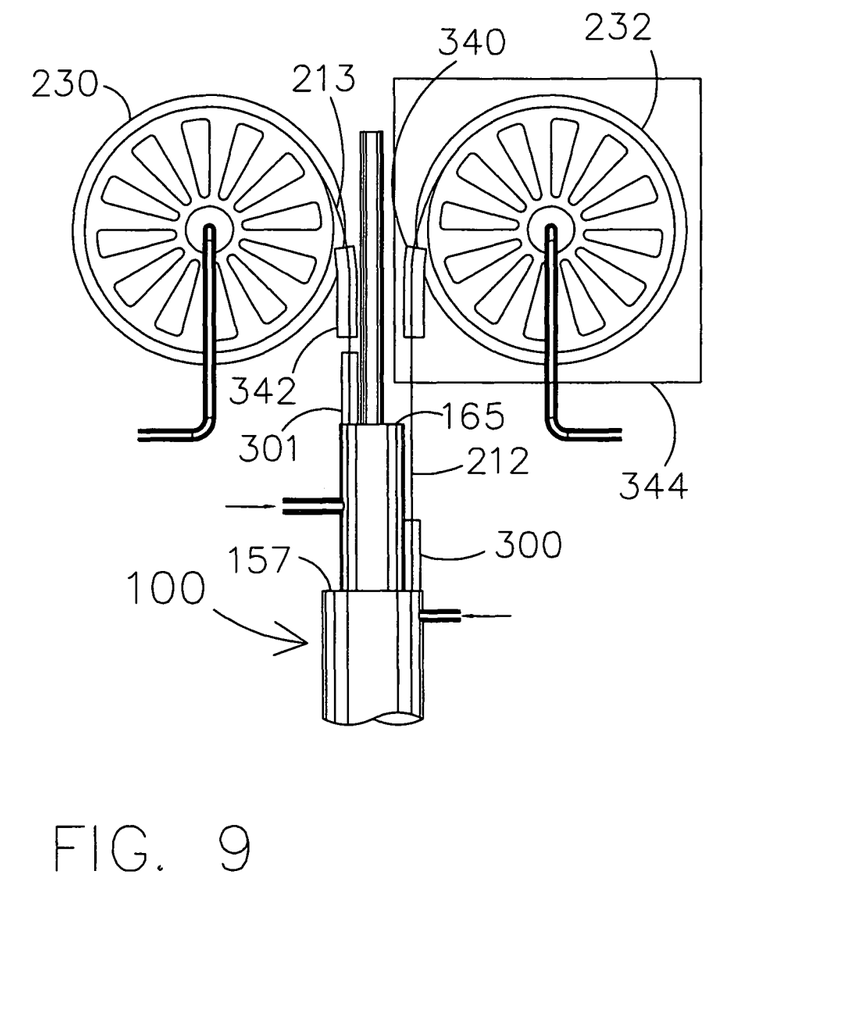
FIG. 9 shows a general side elevational view of the gravity pressure vessel system, showing the reels that serve to drive the tube ribbon assemblies.

This paddle 200 can be employed in both annuli of the gravity pressure vessel, though, ultrasound is preferred only in the downdraft, such that a paddle in the updraft column would preferably include only feed tubes 202, 204 for cleaning, and an anode 210 for cathodic protection. Region 190 is the region most likely suitable for introduction of the ultrasound, at it is best accessed through the downdraft column, annulus 157. It is preferred that at all times at least one paddle from either annulus 157 or annulus 165 will be in the region 190 to introduce ultrasound at the starved oxidation reaction zone. Thus, as seen in FIG. 9, the paddles 200 are fed to the annuli through tube reels 230 and 232 and tube straighteners 342, 340. A tube reel is provided for each tube ribbon assembly 212, and lengths are fed off or wound back on the tube reels to lower or raise the paddle 200 attached thereto. The tubes 202, 204, tubulars 207, 209 and anode 212 are therefore cold worked as they go to and from a straightening device (not shown) between the reels and the gravity pressure vessel. As a result the tubulars must be annealed from time to time to relieve cold working stress, and an annealing chamber 234 is provided for that purpose (only shown on reel 232, with the understanding that such would also be employed for reel 230. The coiled tubing could be heated one at a time to relieve cold working stress that would accumulate upon continually lowering and raising the paddles. For the preferred tubing, which is made from alloy metal, the coil would have to be heated to between 400° C. and 450° C., and any insulation for service wiring would have to be stable at those temperatures. A mineral insulated metal tube jacket wiring would suffice.

Because the paddles are lowered by coiled tubulars, if there is a power failure while a paddle is at a great depth in an annulus, the hanging tubulars of the ribbon assembly could snap back and become entangled with each other or with the pipes forming the annuli of the gravity pressure vessel. To preclude this from happening, it is proposed that the body portion 201 of the paddles be adequately large and heavy to provide ample dead weight to keep the hanging tubulars linear. With the understanding that the gravity pressure vessels of this invention may be from 1600 feet to 2000 feet in height, the body portion 201 is preferably from about 10 to 20 feet in length, with a weight of from 100 to 400 lbs, or, in other embodiments, from 200 to 300 lbs.

Because the cleaning function requires the paddles to travel up and down the annuli of the gravity pressure vessel, while the GPV is operating, it is necessary to provide an apparatus through which the tube ribbon assemblies can be raised and lowered without permitting material to leak from the annuli. This apparatus should also permit for the passage of the paddle itself, for introducing the paddle to the annulus or for removing a paddle there from, for example, for servicing. Running gate assemblies 300, 301 are proposed (FIGS. 8 and 9), and the running gate assembly 300 provided for the tube ribbon assembly 212 entering chamber 157 is the focus for the disclosure thereof, with the understanding that running gate assembly 301 will be structured an will function similarly.

Figure 8:
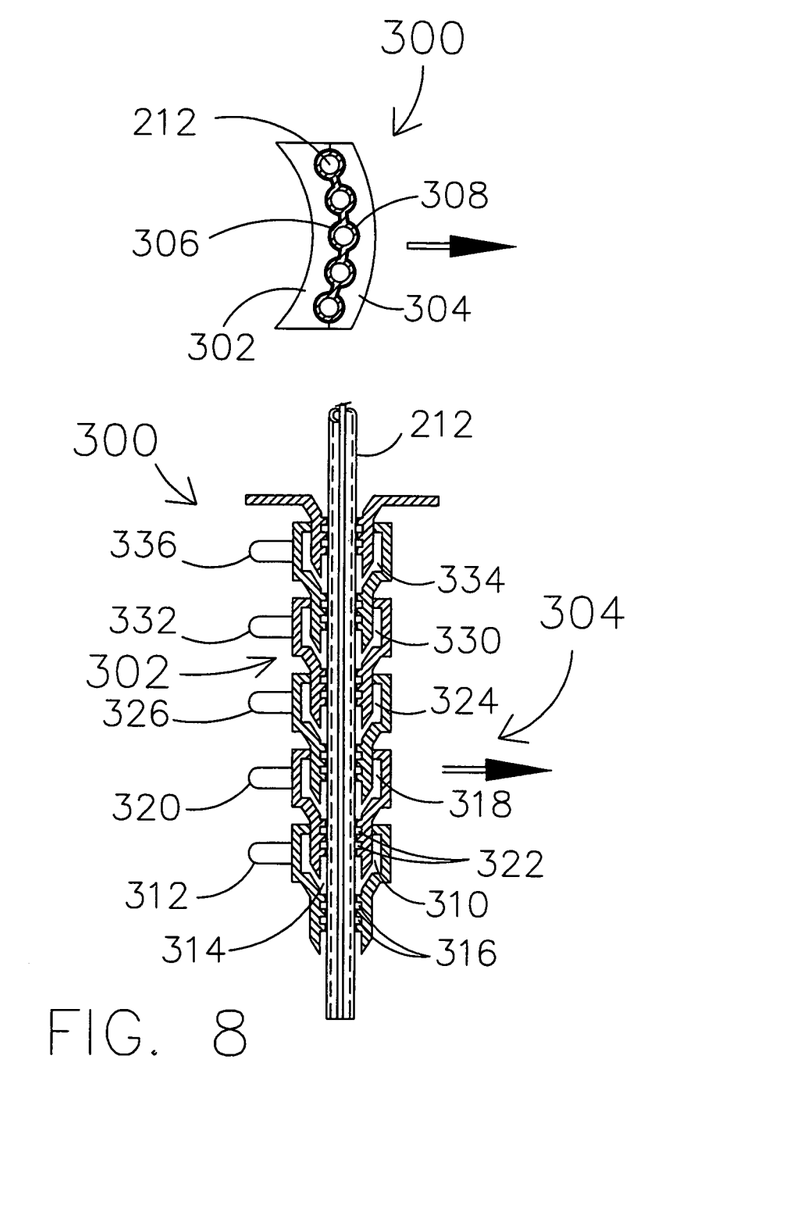
FIG. 8 shows a cross sectional side view and a sectional view of a running gate assembly for a tube ribbon assembly.

In FIG. 8, it can be seen that the running gate assembly 300 includes a fixed anvil 302, providing a concavity 306, and a movable anvil 304, providing a concavity 308, with the concavities 306, 308 defining space for receipt of the tube ribbon assembly 212 when the movable anvil 304 is brought into contact with the fixed anvil 302. The movable anvil might be moved by hydraulic or screw feed or through another suitable mechanism. The fixed anvil 302 and movable anvil 304 are set up in various stages stacked upon each other in order to provide various functions for the running gate assembly 300 as discussed below. The tube ribbon assembly 212 passes upward through a top wall of chamber 157 and enters the first stage 310 of the running gate assembly 300. Air or a gas such as dry carbon dioxide is injected into stage 310 via inlet 312 and creates a moving air wipe through passage 314 in counter-flow against moving tube ribbon assembly 212. The gas is introduced at a pressure that is higher than the pressure in the chamber 157, such that material from chamber 157 will not escape chamber 157 and enter stage 310. It is envisioned that the chamber 157, proximate its top wall, might have a pressure of approximately 2 bar, and the gas would be introduced at stage 310 at approximately 2.2 bar. Gasses from passage 314 then pass down along tube ribbon assembly 212 and are restricted or flow restrained by orifices 316. Continuing upward, the next stage 318 of the running gate assembly 300 is served by a gas extraction outlet 320 which draws gasses past tube ribbon assembly 212 via the orifice sets 322. The pressure at stage 318 is maintained under the pressure in stage 310, below, and stage 324, above. Proceeding with the example started above, a pressure of approximately 1.5 bar is envisioned. In running gate assembly stage 324, clean water is introduced via nozzle 326 against the surfaces of tube ribbon assembly 212. The water is introduced at a pressure higher than that in stage 318, below, and stage 330, above. In the example being giving, a pressure of approximately 1.8 bar is envisioned. The next stage 330 of the running gate assembly is an additional low pressure evacuation zone served by gas extraction outlet 332, and it draws from both stages 324 and 334. In the present example, a pressure of approximately 0.8 bar is envisioned. Stage 334 of the running gate assembly 300 is pressurized to the degree required to preclude the flow of gases or fluids from outside chamber 157 from passing downward through running gate assembly 300 and into chamber 157. Air or a gas such as dry carbon dioxide is injected into stage 334 via inlet 336. It is envisioned that the outside of chamber 157 is the ambient atmosphere, and the pressure to be established in stage 334 would be close to, but slightly above 1 bar, with approximately 1.1 bar being envisioned. In this manner a running gate assembly 300 creates a seal to accommodate the continuous and unrestricted movement of tube ribbon assembly 212 while sustaining segregation of fluids. Any leakage from the system is a controlled leakage of materials introduced at the various stages, and such leakage is acceptable and preferred over leakage from chamber 157 (or chamber 165).

A preferred gravity pressure vessel according to the present invention will have a height from about 1800 feet to about 2200 feet. As with the size of the reactor, the fluid throughput of the reactor is a function of the characteristics of the feedstock. Ideally, the gravity pressure vessel of the present invention will process from about 500 to about 1000 gallons of process stream per hour, with the process stream typically comprising from about 8% and 16% and more commonly between 10% and 14% percent cellulosic material, with the further understanding that the cellulosic material used in accordance with this invention should include significant amounts of woody cellulosic material or even be all woody cellulosic material.

Further details of the pretreatment and post-treatment of the fluids and the treated products of the process and other materials of construction, proportions, cleaning, corrosion and erosion control, catalysts, alternative acids, vent extraction and control of volatile organic compounds, stress strain control, expansion compensation, and the like, would all be known to one normally skilled in the art and are not described herein.

It should thus be evident that the method and apparatus disclosed herein is capable of sustaining conditions amenable to advancing woody cellulosic material through a gravity pressure vessel for the hydrolysis of cellulosic materials in commercial quantities. Although particular apparatus embodiments and process steps have been described here in detail as required, this invention is not particularly limited to or by such embodiments and process steps. Rather any variation evident falls within the scope of the claimed invention and, thus, the selection of specific component elements can be determined without departing from the spirit of the invention herein disclosed and described. The scope of this invention shall include all modifications and variations that may fall within the scope of the claims.

The invention claimed is:

1. A method of hydrolyzing woody cellulosic material containing lignin and air pockets, the method comprising the steps of:
   impregnating the woody cellulosic material with a first alkali having a pH of from 10 to 14 such that the first alkali is in contact with the lignin within the lignin-containing woody cellulosic material and, thereafter, advancing the woody cellulosic material through a gravity pressure vessel whereby the woody cellulosic material is acid hydrolyzed to sugars.

2. The method of claim 1, wherein said step of impregnating includes:
   creating a process stream of the woody cellulosic material and the first alkali as carrier fluid;
   applying a vacuum to the process stream thereby removing air from the air pockets of the woody cellulosic material, and thereafter
   increasing the pressure to which the process stream is subjected such that a portion of the first alkali of the process stream enters air pockets within the woody cellulosic material while the remainder of the first alkali remains as first alkali carrier fluid.

3. The method of claim 2, wherein, after said step of impregnating the woody cellulosic material with a first alkali, the method further comprises the step of substantially removing the first alkali carrier fluid and replacing it with a secondary alkali carrier fluid having a pH of from 7 to 8.5.

4. The method of claim 2, wherein said step of impregnating further comprises:
   subjecting the process stream of the woody cellulosic material and the first alkali to ultrasound.

5. The method of claim 3, wherein said gravity pressure vessel includes:
   a tubular casing having a lower closed end, and
   a counterflow tubular casing positioned within the tubular casing and having an lower open end whereby an outer reaction annulus is formed between the tubular casing and the counterflow tubular casing and a starved oxidation reaction zone is formed proximate the lower closed end of the tubular casing; and
   the method further comprises introducing ultrasound at the starved oxidation reaction zone.

6. The method of claim 5, further comprising adding oxygen proximate the starved oxidation reaction zone.

7. A method of hydrolyzing woody cellulosic material containing lignin and air pockets, the method comprising the steps of:
   introducing woody cellulosic material into a gravity pressure vessel and impregnating the woody cellulosic material with a first alkali having a pH of from 10 to 14, such that the first alkali is in contact with the lignin within the lignin-containing woody cellulosic material, wherein the gravity pressure vessel includes:
   a tubular casing having a lower closed end,
   a counterflow tubular casing positioned within the tubular casing and having an lower open end whereby an outer reaction annulus is formed between the tubular casing and the counterflow tubular casing, and
   a starved oxidation reaction zone proximate the lower closed end of the tubular casing; and
   introducing ultrasound at the starved oxidation reaction zone, whereby the woody cellulosic material is acid hydrolyzed to sugars.

8. The method of claim 7, further comprising adding oxygen proximate the starved oxidation reaction zone.

9. The method of claim 7, wherein said step of impregnating the woody cellulosic material comprises:
   creating a process stream of the woody cellulosic material and the first alkali as carrier fluid;
   applying a vacuum to the process stream thereby removing air from the air pockets of the woody cellulosic material, and thereafter
   increasing the pressure to which the process stream is subjected such that a portion of the first alkali of the process stream enters air pockets within the woody cellulosic material while the remainder of the first alkali remains as first alkali carrier fluid.

10. The method of claim 9, wherein, after said step of impregnating the woody cellulosic material with a first alkali, the step of introducing the cellulosic material further comprises the step of substantially removing the first alkali carrier fluid and replacing it with a secondary alkali carrier fluid having a pH of from 7 to 8.5.

11. The method of claim 9, wherein said step of impregnating further comprises:
   subjecting the process stream of the woody cellulosic material and the first alkali to ultrasound.

12. A method of hydrolyzing woody cellulosic material containing lignin and air pockets, the method comprising the steps of:
- impregnating the woody cellulosic material with a first alkali having a pH of from 10 to 14 such that the first alkali is in contact with the lignin within the woody cellulosic material, and thereafter
- introducing the woody cellulosic material into a gravity pressure vessel, wherein the gravity pressure vessel includes:
  - a tubular casing having a lower closed end,
  - a counterflow tubular casing positioned within the tubular casing and having an lower open end whereby an outer reaction annulus is formed between the tubular casing and the counterflow tubular casing, and
  - a starved oxidation reaction zone proximate the lower closed end of the tubular casing; and
- introducing ultrasound at the starved oxidation reaction zone, whereby, upon advancing the cellulosic material through the gravity pressure vessel, the cellulosic material is acid hydrolyzed to sugars.

\* \* \* \* \*